United States Patent [19]
Keller

[11] Patent Number: 5,122,130
[45] Date of Patent: Jun. 16, 1992

[54] FORCEPS FOR INSERTING INTERVERTEBRAL DEVICE

[75] Inventor: Arnold Keller, Humburg, Fed. Rep. of Germany

[73] Assignee: Waldemar Link GmbH & Co., Hamburg, Fed. Rep. of Germany

[21] Appl. No.: 603,897

[22] Filed: Oct. 25, 1990

Related U.S. Application Data

[62] Division of Ser. No. 323,939, Mar. 14, 1989, Pat. No. 4,997,432.

[30] Foreign Application Priority Data

Mar. 23, 1988 [DE] Fed. Rep. of Germany ....... 3809793

[51] Int. Cl.$^5$ .......................... A61B 17/00; A61F 2/00
[52] U.S. Cl. ....................... 606/61; 606/205; 606/207; 81/302
[58] Field of Search .......... 606/60, 61, 63, 64, 606/99, 205, 206, 207, 208, 209; 81/302, 312, 318, 319, 320, 321, 322, 323, DIG. 6

[56] References Cited

U.S. PATENT DOCUMENTS

| | | |
|---|---|---|
| 717,526 | 1/1903 | Barney ..................... 81/302 |
| 924,426 | 6/1909 | Callahan et al. ............. 81/322 |
| 1,850,268 | 3/1932 | Kulp et al. ................. 81/302 |
| 2,001,707 | 5/1935 | Clemens ..................... 81/302 |
| 3,486,505 | 12/1969 | Morrison . | |
| 4,050,464 | 9/1977 | Hall ........................ 606/61 |
| 4,803,983 | 2/1989 | Siegel ..................... 606/207 |

FOREIGN PATENT DOCUMENTS

| | | |
|---|---|---|
| 0176728 | 4/1986 | European Pat. Off. . |
| 0269935 | 6/1988 | European Pat. Off. . |
| 1065565 | 9/1959 | Fed. Rep. of Germany ...... 606/207 |
| 3023942 | 1/1982 | Fed. Rep. of Germany . |
| 0363346 | 7/1906 | France ..................... 606/207 |
| 0219095 | 5/1968 | U.S.S.R. ................... 606/207 |
| 0248155 | 7/1969 | U.S.S.R. ................... 606/207 |

OTHER PUBLICATIONS

Eine Alternative Behandlungsstrategie beim lumbalen Bandscheibenschaden mit der Bandscheiben-endoprothese Modulartyp SB Charite, Karin Buttner-Janz et al, Z. Orthop. 125 (1987) 1-6.
European Search Report for EP 89 10 1147.

Primary Examiner—Max Hindenburg
Assistant Examiner—Glenn K. Dawson
Attorney, Agent, or Firm—Chilton, Alix & Van Kirk

[57] ABSTRACT

A spreading forceps (9) which has, at its front end on each spreading jaw (10, 11), an essentially U-shaped recess surrounding one stop plate on three sides and gripping the edge, the thickness of the spreading jaws (10, 11) in the spreading direction being essentially identical to the thickness of the stop plates (FIG. 1). The spreading forceps is useful for the insertion of intervertebral endoprostheses.

21 Claims, 5 Drawing Sheets

FORCEPS FOR INSERTING INTERVERTEBRAL DEVICE

RELATED U.S. APPLICATION DATA

This application is a division of U.S. patent application Ser. No. 323,939, filed Mar. 14, 1989, now U.S. Pat. No. 4,997,432.

DESCRIPTION

The invention relates to a surgical instrument set for the insertion of intervertebral endoprostheses, which consist of two stop plates and a sliding core to be arranged between them.

It is known to replace intervertebral discs in the spinal column, which have become pathologically changed or are no longer able to function, by intervertebral endoprostheses (Article by Büttner-Janz, K., Schellnack, K., Zippel, H. "Eine alternative Behandlungsstrategie beim lumbalen Bandscheibenschaden mit der Bandscheibenendoprothese Modulartyp SB Charité" [An alternative treatment strategy for lumbar intervertebral disc lesion using the SB Charité modular type intervertebral disc endoprothesis], Z. Orthop. 125 (1987), 1-6). These intervertebral endoprostheses are inserted between the vertebrae in place of the previously removed intervertebral disc. The two stop plates in this case have toothed projections by means of which they are secured to the vertebral bodies. On their surfaces facing towards each other they have spherical-shell-shaped recesses between which is positioned a sliding core which has similarly formed spherical-shell-shaped projections. In this way, following the operation, a relative movement of the vertebrae to each other is again possible. The stop plates of the endoprostheses in this case consist of metal, while the sliding core consists of synthetic material.

A major problem arises on insertion of these intervertebral endoprostheses. In order to be able to insert the intervertebral endoprostheses, the vertebral bodies situated opposite each other must be spread apart from each other. However, the use of known spreading forceps, which are normally used for operations on the intervertebral disc, would occupy the position which the intervertebral endoprosthesis is intended to assume. In this connection it should be noted that the intervertebral endoprosthesis should, for the purpose of favourable load distribution, be supported over as large an area as possible, corresponding to the size of the vertebral bodies. Similarly, the spreading apart of the vertebral bodies situated opposite each other necessitates considerable forces.

Thus, with the hitherto conventional spreading forceps, it would only be possible at most to grip the vertebral bodies by the outer edges which are not occupied by the intervertebral endoprosthesis. These only limited bone surfaces of the vertebral bodies would, however, be too small for the application of the necessary forces and would therefore give rise to the risk of the vertebral bodies collapsing at these points.

The object of the invention consists in the provision of an instrument set, with which the endoprostheses can be inserted with simultaneous spreading of the vertebral bodies and as small a risk as possible of the vertebral bodies collapsing.

The solution according to the invention consists in the instrument set having spreading forceps which have, at their front end on each spreading jaw, an essentially U-shaped recess surrounding one stop plate on three sides and gripping the edge, the thickness of the spreading jaws in the spreading direction being essentially identical to the thickness of the stop plates.

The stop plates are thus surrounded on three sides by the spreading jaws. Here, the two stop plates at first lie directly on each other. In this position the spreading jaws are then brought between the two vertebral bodies. Subsequently the spreading takes place so that space is created for the sliding core, in which respect the spreading must be effected to a still greater extent since the sliding core must at first be introduced between the stop plates with its projections.

The considerable forces arising in this respect are not transmitted only to small regions of the vertebral bodies, but over a large area. This force is here exerted by the stop plates. In this manner the collapsing of the vertebral bodies is prevented with as large a degree of certainty as possible. The vertebral bodies come into contact essentially only with the parts with which they are also in contact following the operation, namely the stop plates.

The spreading jaws are expediently provided, in the area of the inner sides of the legs of the U, with grooves for receiving the stop plates, which grooves are arranged in the plane perpendicular to the spreading direction. The stop plates can thereby be pushed from the open end of the U laterally into the spreading jaws. The large spreading forces exerted on the stop plates are in this case absorbed by the side walls of the grooves. The force here only acts in one direction, so that only one groove wall need be designed with special strength. The outer groove wall must only be to prevent the falling-out of the stop plates. Here the groove walls can be designed weaker, it being possible for the grooves to have bevelled walls, since then the stop plates can also have correspondingly bevelled walls at the corresponding positions, so that no sharp edges are present here.

So that the stop plates cannot slip forward out of the opening of the U, a resiliently yielding catch can be provided at a front groove end of each spreading jaw. When a stop plate is pushed into the spreading jaw, the resiliently yielding catch prevents the same from falling out. If, on the other hand, the endoprosthesis is inserted, the catch will yield when it is desired to withdraw the forceps.

During the spreading procedure it is expedient for the stop plates to be moved apart from each other in such a way that their surfaces touching the vertebral bodies remain parallel. It is therefore expedient for the spreading jaws to be connected to a scissor-like parallel guide.

It will be expedient for the spreading forceps to have a detachable notch device for the spread position so that, after the spreading, the hands of the operating surgeon are free to insert the sliding core.

Pushing the spreading forceps, together with the stop plates arranged thereon, between the vertebral bodies requires a relatively large amount of force which can be transmitted only very poorly or not at all by the spreading forceps alone. It is therefore expedient for the spreading forceps to be provided, in the area of the spreading jaws, with a projection or a recess, which projection or recess has a contact surface, oriented essentially transverse to the driving-in direction, for an essentially rod-shaped driving-in instrument. The force for pushing the spreading forceps in is thus applied with the aid of a driving-in instrument, by means of which the driving-in force can be exerted in the correct direction, which is not possible especially in the case of bent spreading jaws. The contact surface can in this context have a cylindrical or spherical cross-section, so that the driving-in instrument can be applied at different angles.

As already mentioned, the spreading forces are very great. Since the spreading forceps have relatively long levering arms, they would become very unwieldy if they were designed so stable that they could exert the necessary spreading forces in every case. It is therefore expedient for the instrument set to have an essentially screwdriver-like rod-shaped element which bears, at its one end, a hand grip, the other end having the form of an oblong plate. Once the spreading has been begun and the spreading jaws have already reached a certain distance from each other, the rod-shaped element can be introduced between the jaws in such a way that the plane of the oblong plate is essentially parallel to the plane of the spreading jaws. If the rod-shaped element is then subsequently turned, a very great force is exerted exactly at the position where the spreading force is required, until the plane of the plate is essentially perpendicular to the plane of the spreading jaws. In this position the rod-shaped element can then remain in the spreading forceps, in order to fix this position. Where appropriate, this spreading can be progressively extended by subsequently using a rod-shaped element with a somewhat wider plate, so as to in this way gradually obtain greater widths.

Instead of a plate with an essentially rectangular cross-section and rounded-off edges, it would also be possible, for example, to use an oval part.

The sliding cores can be particularly expediently inserted if the instrument set has a holding instrument for sliding cores, which holding instrument is rod-shaped and is provided, at the front end, with resilient holding elements surrounding the sliding core at the periphery over an angular range of somewhat more than 180°.

The resilient holding elements initially hold the sliding core secure. Once the spreading is ended and the sliding core is held secure between the stop plates, the holding instrument can be withdrawn again, the holding elements detaching from the sliding core by virtue of their spring action, and the sliding core remaining in the desired position.

It is expedient to provide two holding elements which are connected integral with each other, extend in each case over an angular range of approximately 90° and are connected to a bar which extends through the holding instrument designed in tube form, with the holding elements bearing against the inside of the tube end by means of oblique surfaces diverging from each other towards the front, and with a screw arrangement being provided at the other end for exerting a tensile force on the bar. In this embodiment form the two holding elements are forced apart from each other as a result of the spring effect, so that an opening is formed into which the sliding core can be introduced. If a tensile force is subsequently exerted on the bar, then the oblique surfaces touch the inside of the tube so that the holding elements are pressed towards each other counter to the spring force and thereby secure the sliding core. So that the sliding core can subsequently be removed from the holding instrument or the holding instrument withdrawn from the sliding core, the tensile force then simply has to be cancelled by turning the screw arrangement in the opposite direction.

The holding instrument is to be used particularly expediently in connection with the spreading forceps, but can also be used for other types of insertion of endoprostheses. The invention therefore also relates to an instrument set which has only one or several holding instruments.

If the instrument set additionally has a bar-shaped element at the front of which a model of a sliding core is attached, once the spreading has been carried out it can then be determined, by means of these elements, which sliding core is most suitable. For this purpose, several such bar-shaped elements will of course be used with different sliding cores. The correct size is thus tested using models of sliding cores and not using sliding cores of which one is then subsequently intended to remain in the endoprosthesis. This is more expedient, inter alia, for reasons of sterilization, since a sliding core remaining in the body for a long period must be sterilized more carefully than a model of a sliding core which will be removed again after a short time.

It is expedient for the instrument set to have not only several bar-shaped elements with models of sliding cores, but also several spreading forceps, screwdriver-like spreading elements and holding instruments for sliding cores, so that endoprostheses of different sizes can be inserted.

The invention is described below on the basis of advantageous embodiments and with reference to the attached drawings in which.

Figure 1:
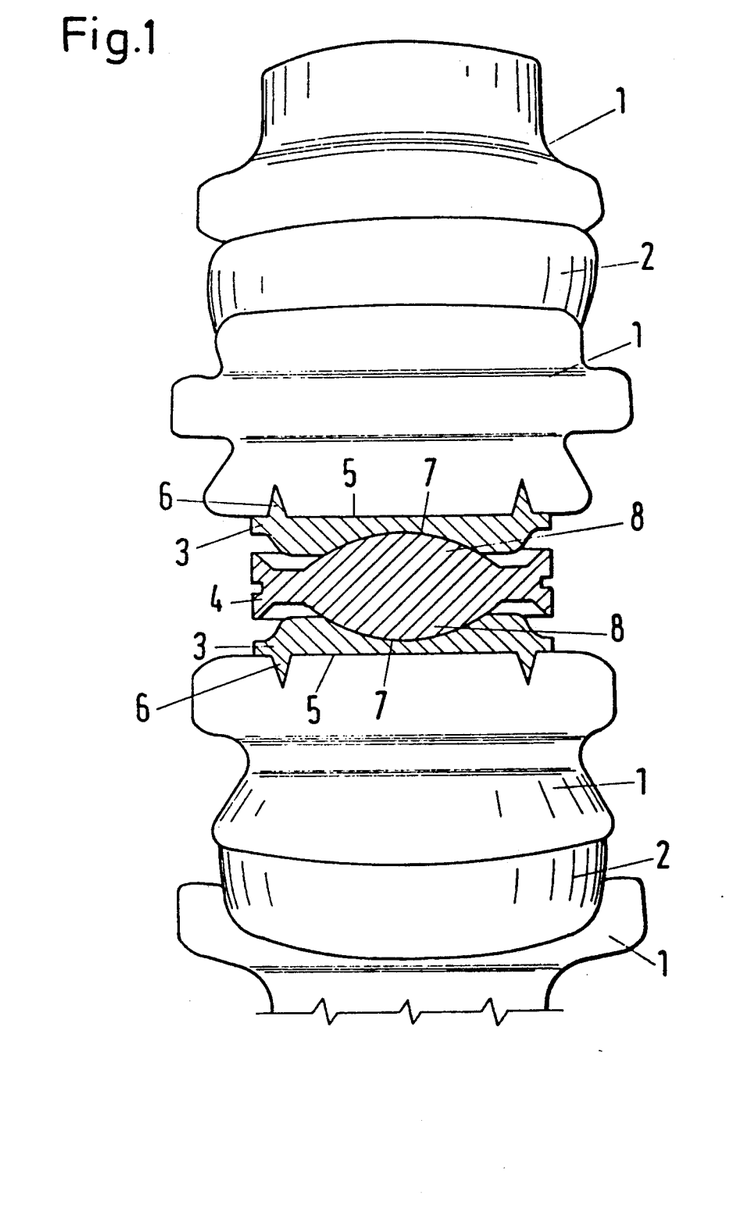
FIG. 1 shows, in cross-section, an intervertebral endoprosthesis which can be inserted using the instrument set according to the invention.

FIG. 1 shows in cross-section a part of a spinal column with an endoprosthesis inserted therein. The spinal column consists of a plurality of vertebral bodies 1 between which, in healthy humans, intervertebral discs 2 are arranged. The intervertebral disc between the two middle vertebral bodies 1 is replaced by the intervertebral endoprosthesis which can be used in connection with the instrument set according to the invention. The endoprosthesis consists of two stop plates 3 and a sliding body 4 arranged between these. On the side directed towards the vertebral body 1 the stop plate 3 has an essentially plane surface 5 provided with tooth-like projections 6 which penetrate into the vertebral body in order to fix the stop plates 3 securely to the vertebral body 1. On the opposite side the stop plates 3 are provided with an essentially spherical-shell-shaped recess 7. The stop plates 3 normally consist of metal.

Arranged between the stop plates 3 is the sliding core 4, which has spherical-shell-shaped projections 8 corresponding to the spherical-shell-shaped recesses 7. The sliding body 4 normally consists of synthetic material.

The spreading forceps 9 shown in FIGS. 2 to 6 have two spreading jaws 10, 11 which are arranged in parallel and which can be spread apart from each other by a scissor-like articulation 12 with the aid of levers 13, 14 in such a way that their surfaces remain parallel. The levers 13, 14 are here forced apart from each other by springs 15, so that the spreading jaws 10, 11 are normally pressed together. If the levers 13, 14 are pressed together counter to the force of the spring 15, then the spreading jaws 10, 11 are forced apart. The teeth of a locking element 16, which is spring-loaded clockwise by a spring 17 in FIG. 2, engage in corresponding teeth or projections in the lower lever 14, so that the spreading position obtained in each particular case is maintained by the element 16, which is attached pivotably on the lever 13.

Figures 2, 3:
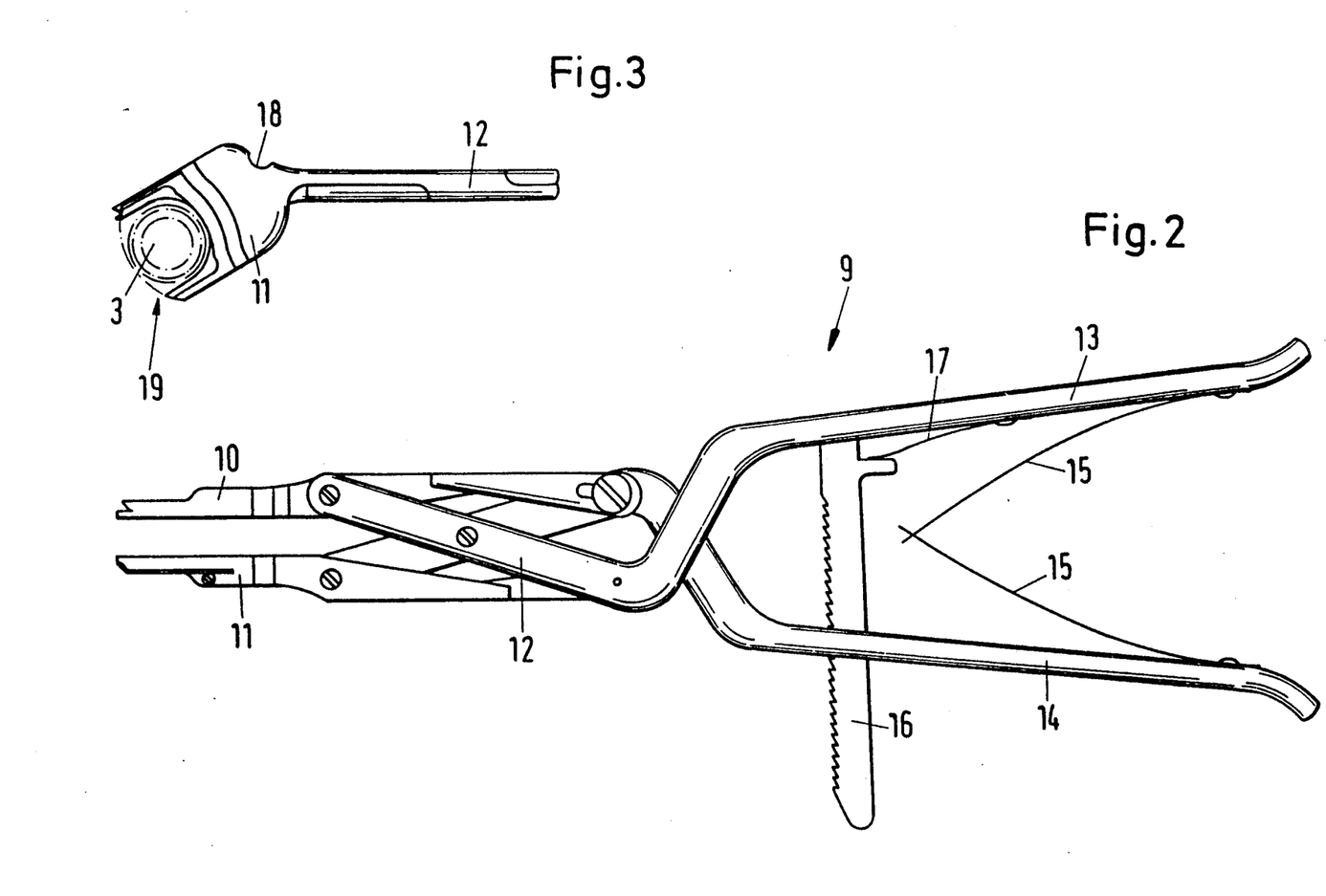
FIG. 2 shows spreading forceps according to the invention in side view.
FIG. 3 shows a detail of the spreading forceps of FIG. 2 in plan view.
Figure 10:
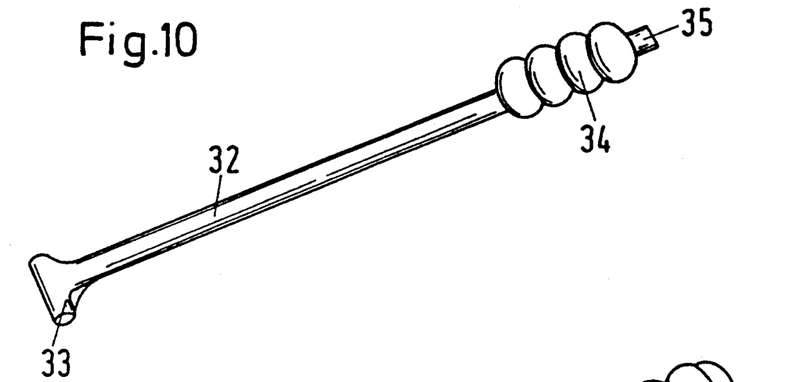
FIG. 10 shows a driving-in instrument which can be used with the spreading forceps in FIGS. 2 to 6.

As can be seen in FIG. 3, the spreading jaws 10, 11 are angled relative to the longitudinal direction of the forceps, since in this way the spreading jaws can be better introduced into the free space between the vertebral bodies. Since great forces are normally required for this purpose, the spreading jaws 10, 11 have, at their rear end, a cylinder-shaped recess 18 in which a driving-in instrument can be applied, which driving-in instrument is shown in FIG. 10.

The spreading jaws 10, 11 have, at their front end, a U-shaped recess 19 into which a stop plate 3 can be inserted. In the cross-sectional view in FIG. 5 only one of these stop plates 3 is shown. The stop plates 3 are held in grooves 20 which extend along the legs of the U. The stop plates 3 are thus only held by the edge in corresponding grooves 20 of the spreading jaws 10, 11, which grooves are bevelled on one side. However, at the side on which the greatest force is exerted by the stop plates 3, the groove base is level and essentially parallel to the plane of the spreading jaws.

Figures 4, 6:
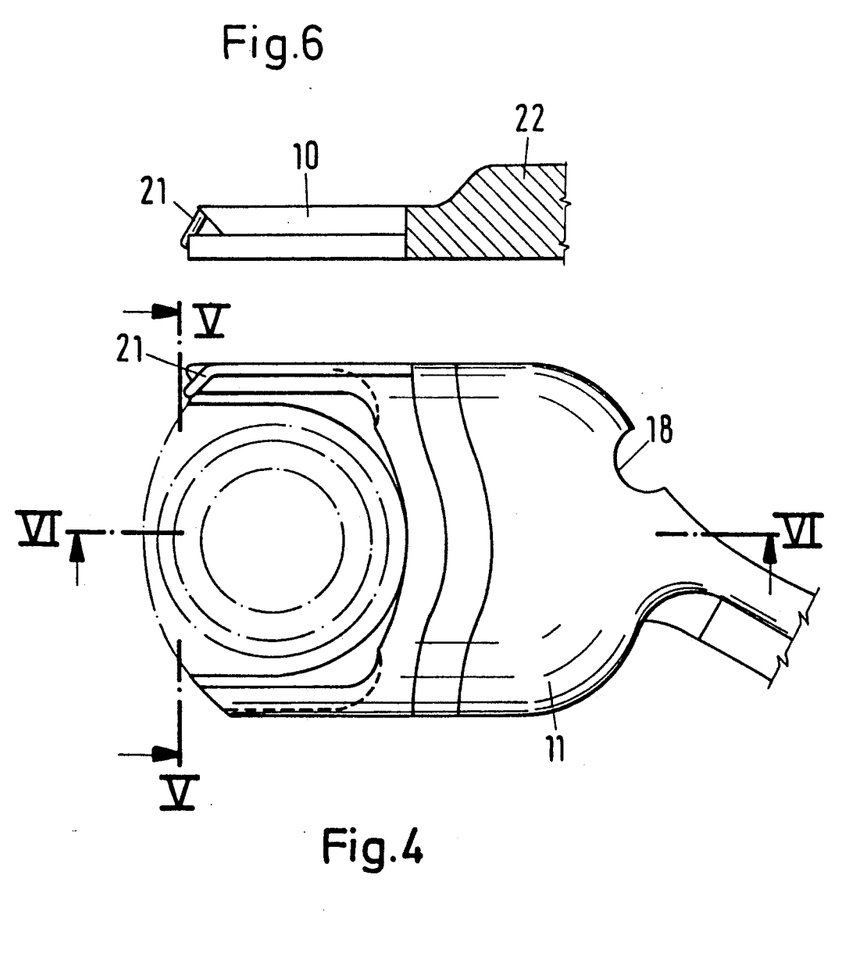
FIG. 4 shows an enlarged representation of the part in FIG. 3.
FIG. 6 shows a cross-sectional view along the line VI—VI in FIG. 4.
Figure 5:
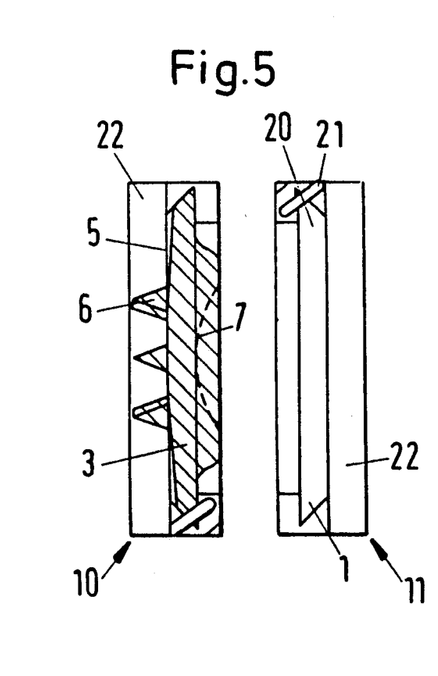
FIG. 5 shows a cross-sectional view along the line V—V in FIG. 4.

FIGS. 4 to 6 also show a spring catch 21 which normally closes the groove exit and thereby secures a stop plate 3 enclosed therein. This spring catch 21 does however yield when it is desired that a stop plate be inserted into the groove 20 or the spreading forceps withdrawn after introduction of the endoprosthesis.

As can be seen in FIGS. 4 to 6, the spreading jaws 10, 11 have, in the front part which is brought between the vertebral bodies, essentially the thickness of the stop plates 3. The teeth 6 here project above this area. Only behind the area of the spreading jaws which is introduced between the vertebral bodies do the spreading forceps have a thickened portion 22 increasing the stability.

Figure 7:
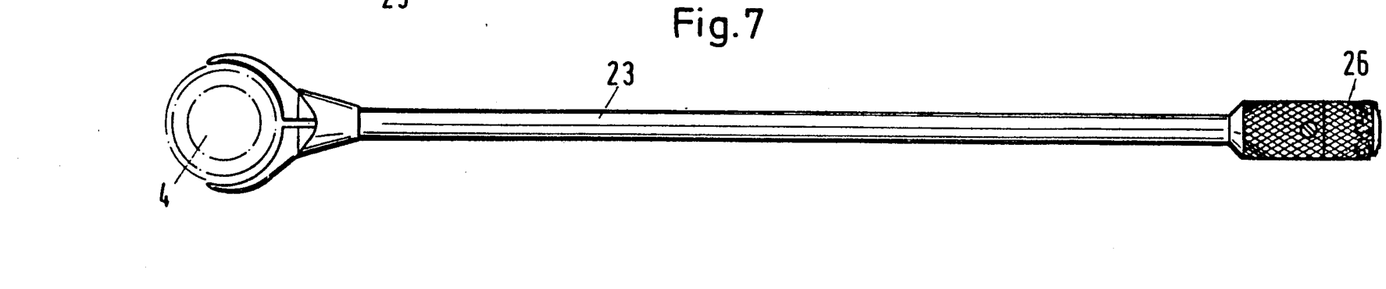
FIG. 7 shows an overall view of a holding instrument for sliding cores.
Figure 8:
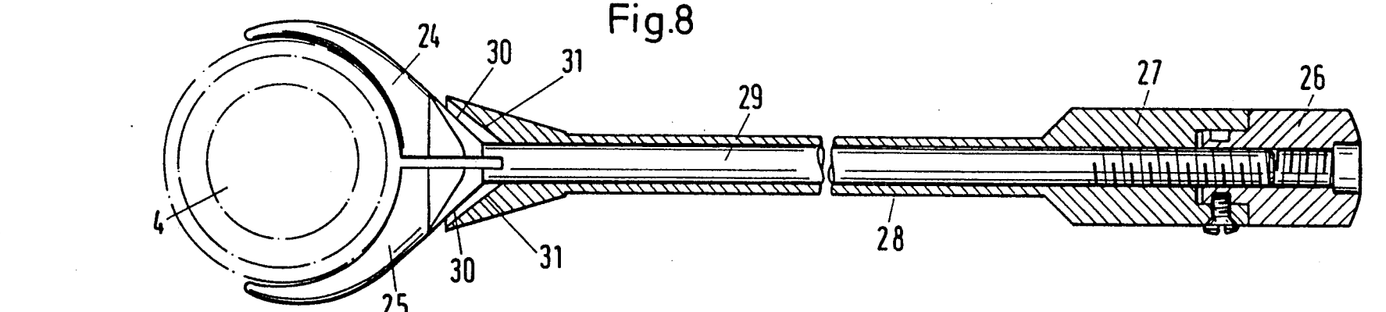
FIGS. 8 and 9 show cross-sectional views of the instrument in FIG. 7 in different work positions.
Figure 9:
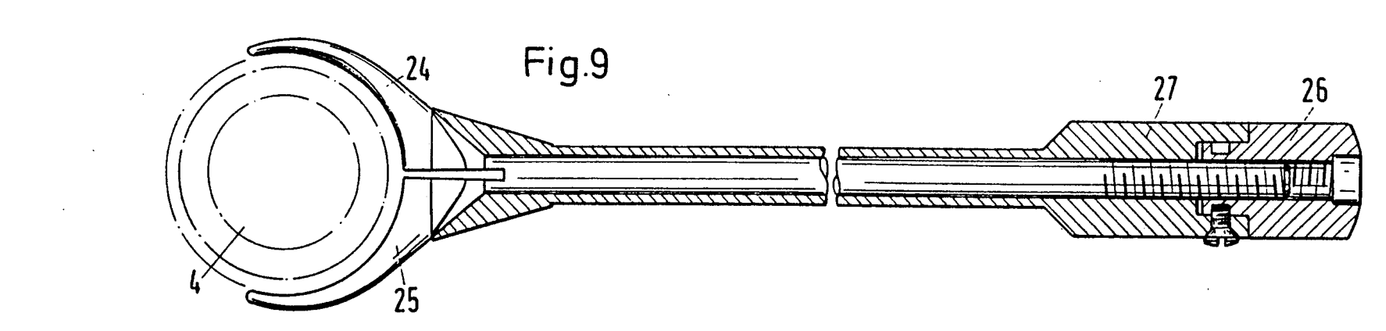

FIG. 7 to 9 show a holding instrument 23 for sliding cores 4. FIG. 7 is a projection. FIGS. 8 and 9 are cross-sectional representations in two different operating positions.

The holding instrument 23 has an essentially U-shaped holding element which consists of two legs 24, 25. The legs normally assume the rest position shown in FIG. 8, in which the legs 24, 25 embrace the sliding core 4 only relatively loosely. If, however, the screw 26 at the rear end of a hand grip 27 is turned, then a tensile force is exerted on a drawbar 29 which is arranged in an outer tube 28 and is connected to the holding element parts 24, 25. In this way the holding element parts 24, 25 with bevelled surfaces 30 push against corresponding bevelled surfaces 31 of the tube 28 or of an attachment to the same, so that the two parts 24, 25 are pressed together and hold the sliding core 4 securely.

FIG. 10 shows a driving-in instrument 32 which is designed essentially rod-shaped. At its front end it bears a transverse cylindrical part 33, which can be inserted into the recess 18 of the spreading forceps 9 in FIGS. 2 to 4. If the driving-in instrument 32 is then held securely at the hand grip 34 and an impact force is exerted on the end 35 opposite the cylindrical part 33, then the spreading forceps 9 can, together with the stop plates arranged thereon, be introduced into the space between the vertebral bodies.

Figure 11:
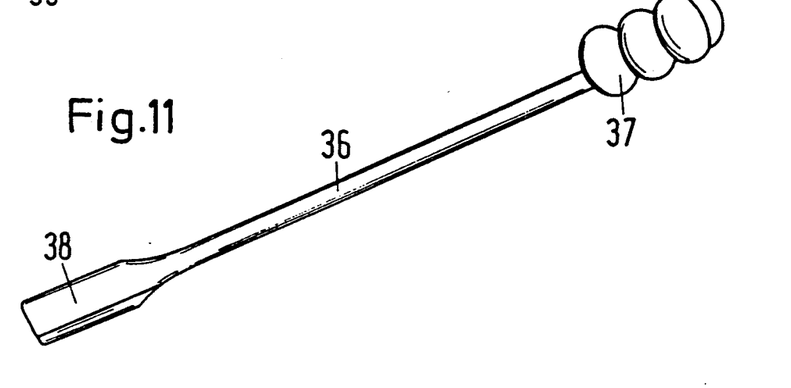
FIG. 11 shows an additional screwdriver-shaped spreading instrument.

Once the spreading has been carried out to a certain extent, further spreading can be effected using the instrument 36 in FIG. 11. This instrument 36 likewise has a hand grip 37 and at the other end is widened in the manner of a screwdriver to form a plate 38. This plate 38 is introduced between the spreading jaws in a position in which the plane of the plate 38 is arranged essentially parallel to the plane of the spreading jaws or at least does not include too great an angle. The spreading jaws can then be forced further apart by turning the instrument 36.

Figure 12:
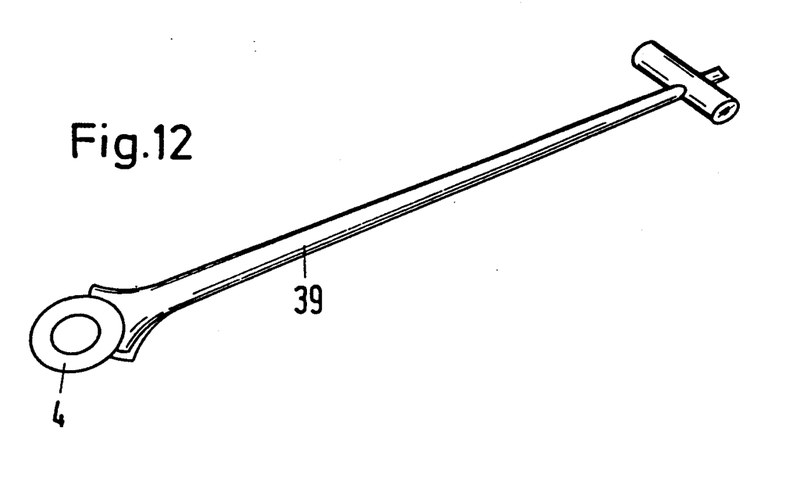
FIG. 12 shows a bar-shaped element with a model of a sliding core.

Finally, FIG. 12 also shows a bar-shaped element 39 which, at the front, bears the model of a sliding core 4. Using the instrument 39 tests can be carried out to determine which size of sliding core is most suitable.

I claim:

1. A surgical forceps for applying pressure against a vertebral body, said forceps having a back portion and a front portion including a front end, the front portion being formed as first and second spreading jaws that are substantially parallel when in a spread position, each spreading jaw having a substantially U-shaped recess having an open portion directed towards front end of the forceps, each U-shaped recess being defined in a plane substantially parallel to the other jaw and perpendicular to the spreading direction and including an inner wall having a groove arranged in a plane substantially perpendicular to the spreading direction.

2. A surgical forceps according to claim 1, wherein at least one groove has bevelled side walls.

3. A surgical forceps according to claim 1, wherein the spreading jaws are connected to scissor-like first and second levers, the levers being connected to the spreading jaws such that the spreading jaws move apart when the first and second levers move toward each other.

4. A surgical forceps according to claim 3, wherein the surgical forceps have a detachable notched device for holding a selected spread position of the spreading jaws, the notched device being connected to the first and second levers.

5. A surgical forceps according to claim 1, wherein the surgical forceps are provided, in the area of the spreading jaws, with means defining a contact surface for engaging a substantially rod-shaped driving-in instrument.

6. A surgical forceps according to claim 1, wherein the inner wall of each U-shaped recess includes a center portion and two leg portions, and each groove includes a pair of grooves formed on the leg portions.

7. A surgical forceps for applying pressure against a vertebral body, said forceps having a back portion and a front portion including a front end, the front portion being formed as first and second spreading jaws, each spreading jaw having a substantially U-shaped recess defined in a plane substantially parallel to the other jaw and perpendicular to the spreading direction, the U-shaped recess having an opening in the direction of the front end and having a groove arranged in a plane substantially perpendicular to the spreading direction and parallel to the U-shaped recess, wherein at least one groove has bevelled side walls.

8. A surgical forceps according to claim 7, wherein on each spreading jaw, a resiliently yielding catch is provided at the front end of the forceps proximate the groove.

9. A surgical forceps according to claim 7, wherein the spreading jaws are connected to scissor-like first and second levers, the levers being connected to the spreading jaws such that the spreading jaws move apart when the first and second levers move toward each other.

10. A surgical forceps according to claim 9, wherein the surgical forceps have a detachable notched device for holding a selected spread position of the spreading jaws, the notched device being connected to the first and second levers.

11. A surgical forceps according to claim 7, wherein the surgical forceps are provided, in the area of the spreading jaws, with means defining a contact surface for engaging a substantially rod-shaped driving-in instrument.

12. A surgical forceps according to claim 7, wherein each U-shaped recess includes a center portion and two leg portions, and each groove includes a pair of grooves formed on the leg portions.

13. A surgical forceps for applying pressure against a vertebral body, said forceps having a back portion, and a front portion including a front end, the front portion comprising two opposed, elongated substanially parallel spreading jaws, each jaw having a substantially U-shaped recess including an inner wall having a groove, the recess and groove being defined in a plane perpendicular to the spreading direction, the recess being open in the direction of the front end of the forceps.

14. A surgical forceps according to claim 13, wherein at least one groove has bevelled side walls.

15. A surgical forceps according to claim 13, wherein on each spreading jaw, a resiliently yielding catch is provided at the front end of the forceps proximate the groove.

16. A surgical forceps according to claim 13, wherein the spreading jaws are connected to scissor-like first and second levers, the levers being connected to the spreading jaws such that the spreading jaws move apart when the first and second levers move toward each other.

17. A surgical forceps according to claim 16, wherein the surgical forceps have a detachable notched device for holding a selected spread position of the spreading jaws, the notched device being connected to the first and second levers.

18. A surgical forceps according to claim 13, wherein the surgical forceps are provided, in the area of the spreading jaws, with means defining a contact surface for engaging a substantially rod-shaped driving-in instrument.

19. A surgical forceps for applying pressure against a vertebral body, the forceps having a back portion and a front portion including a front end, the front portion being formed as first and second substantially parallel spreading jaws, each spreading jaw having a substantially U-shaped recess defined in a plane substantially parallel to the other jaw and perpendicular to the spreading direction, the U-shaped recess including an open portion directed towards the front end of the forceps, wherein each jaw has a resiliently yielding catch at the front end of the forceps.

20. A surgical forceps according to claim 19, wherein the spreading jaws are connected to scissor-like first and second levers, the levers being connected to the spreading jaws such that the spreading jaws move apart when the first and second levers move toward each other.

21. A surgical forceps according to claim 20, wherein the surgical forceps have a detachable notched device for holding a selected spread position of the spreading jaws, the notched device being connected to the first and second levers.

* * * * *

UNITED STATES PATENT AND TRADEMARK OFFICE
CERTIFICATE OF CORRECTION

PATENT NO. : 5,122,130

DATED : June 16, 1992

INVENTOR(S) : Arnold Keller

It is certified that error appears in the above-identified patent and that said Letters Patent is hereby corrected as shown below:

The portion of the term of this patent subsequent to March 5, 2008, has been disclaimed.

Signed and Sealed this

Sixth Day of October, 1992

Attest:

DOUGLAS B. COMER

Attesting Officer

Acting Commissioner of Patents and Trademarks